(12) United States Patent
Yang et al.

(10) Patent No.: US 11,975,198 B2
(45) Date of Patent: May 7, 2024

(54) NERVE STIMULATOR AND MANUFACTURING METHOD THEREOF

(71) Applicant: HANGZHOU NANOCHAP ELECTRONICS CO., LTD., Hangzhou (CN)

(72) Inventors: Jiawei Yang, Hangzhou (CN); Nhan Tran, Hangzhou (CN); Xuyan Yang, Hangzhou (CN)

(73) Assignee: HANGZHOU NANOCHAP ELECTRONICS CO., LTD., Hangzhou (CN)

(*) Notice: Subject to any disclaimer, the term of this patent is extended or adjusted under 35 U.S.C. 154(b) by 827 days.

(21) Appl. No.: 16/962,749

(22) PCT Filed: May 16, 2018

(86) PCT No.: PCT/CN2018/087065
§ 371 (c)(1),
(2) Date: Jul. 16, 2020

(87) PCT Pub. No.: WO2019/140816
PCT Pub. Date: Jul. 25, 2019

(65) Prior Publication Data
US 2020/0353259 A1    Nov. 12, 2020

(30) Foreign Application Priority Data

Jan. 17, 2018 (CN) .......................... 201810043984.X

(51) Int. Cl.
*A61N 1/04* (2006.01)
*A61N 1/05* (2006.01)
(Continued)

(52) U.S. Cl.
CPC ....... *A61N 1/36125* (2013.01); *A61N 1/0476* (2013.01); *A61N 1/0543* (2013.01);
(Continued)

(58) Field of Classification Search
CPC .. A61N 1/0456; A61N 1/0476; A61N 1/0492; A61N 1/0543; A61N 1/0551;
(Continued)

(56) References Cited

U.S. PATENT DOCUMENTS

2015/0371929 A1* 12/2015 Tai ...................... H01L 23/4985
                                                                      623/6.63
2017/0007813 A1*  1/2017 Negi .................... A61B 5/6868

* cited by examiner

*Primary Examiner* — Carl H Layno
*Assistant Examiner* — Jane C Kalinock
(74) *Attorney, Agent, or Firm* — HAUPTMAN HAM, LLP

(57) ABSTRACT

A nerve stimulator and a manufacturing method thereof. The nerve stimulator includes a glass substrate, and a plurality of metal pins provided on the substrate, wherein the metal pins form stimulation portions on one side of the substrate, and the density of the metal pins is greater than 15 Pin/mm². The stimulation portions in the present nerve stimulator have a high density and a good stimulation effect. The processing method thereof is to cut out a high-density metal pin array first by using a metal underlayer, then the manufacturing method overcomes the deficiency in the prior art that it is rather difficult to manufacture a high density of nerve stimulation electrodes by using other substrates such as ceramics and the like.

5 Claims, 3 Drawing Sheets

(51) Int. Cl.
*A61N 1/36* (2006.01)
*B23K 26/38* (2014.01)
*C03C 27/02* (2006.01)
*H05K 1/03* (2006.01)
*H05K 1/11* (2006.01)

(52) U.S. Cl.
CPC .............. *B23K 26/38* (2013.01); *C03C 27/02* (2013.01); *H05K 1/0306* (2013.01); *H05K 1/11* (2013.01)

(58) Field of Classification Search
CPC .............. A61N 1/3605; A61N 1/36014; A61N 1/36125; B23K 26/38; C03C 27/02; H05K 1/0306; H05K 1/11
USPC ......................................................... 607/115
See application file for complete search history.

NERVE STIMULATOR AND MANUFACTURING METHOD THEREOF

RELATED APPLICATIONS

The present application is a National Phase of International Application Number PCT/CN2018/087065, filed May 16, 2018, and claims the priority of China Application No. 201810043984.X, filed Jan. 17, 2018.

TECHNICAL FIELD

The present invention relates to the field of medical devices, and specifically to a nerve stimulator and a manufacturing method thereof.

BACKGROUND

Micro-electrode stimulator, as an important tool for the treatment of neurological diseases, has attracted more and more attention from people, and has become an important research direction at present. In the existing retinal micro-electrode stimulator, the simulation electrode is generally adopts flexible MEMS technology and the stimulation electrode; the wiring; and the pad for flip-chip bonding with the ceramic substrate are integrally formed. However, flexible micro-electrode wiring is generally wired one by one from the stimulation electrode to the outside of an eyeball. When the number of stimulation electrodes is too large, the number of wirings also increases, and a considerable number of wirings would result in an increased diameter of a connecting flat cable, making the postoperative trauma larger.

There are also some stimulation electrodes made of rigid materials. These stimulation electrodes are produced by punching holes in a substrate and then embedding stimulation micro-pins in the holes. Generally, it is rather difficult to process such stimulation electrodes made of rigid materials to form a stimulation electrode array with a density exceeding 5 Pin/mm$^2$.

In medical treatment, the greater the density of the stimulation electrodes is, the better the stimulation effect can be achieved on a smaller substrate, but how to make a high-density stimulation electrode array has always been a problem in the industry.

SUMMARY

In order to solve the above-mentioned defects of too small density of stimulation electrodes, poor stimulation effect and the like, the present invention provides a brand-new nerve stimulator and a method for manufacturing the same. In the nerve stimulator in the present invention, a high-density metal stimulation array can be produced on a substrate, and a chip can be connected onto the substrate to avoid the problem of requiring a large number of wires to be connected to the outside of an eyeball to increase the surgical trauma. The specific solutions are as follows.

Firstly, the present invention claims a nerve stimulator, comprising a substrate, a plurality of metal pins provided on the substrate, wherein the metal pins form stimulation portions on one side of the substrate, the substrate is made of a glass material and a pad structure made of a metal material further provided on the glass substrate. In the present invention, the substrate is made of a brand-new glass material, and the stimulation electrodes are made of a metal material. The materials of the present nerve stimulator are quite different from those of traditional stimulation electrodes, and are easy for processing.

Preferably, the density of the metal pins is greater than 15 Pin/mm$^2$. The greater the density, the better the stimulation effect will be. The specific density of the metal pins can be adjusted according to actual needs, and since the metal pins are formed by processing in a manner of cutting metal, the density thereof can be adjusted in a quite broad range.

Preferably, the height of the stimulation portion is 1 μm to 100 μm.

Preferably, the stimulation portion has the shape of an elongated pyramid.

Preferably, the pad structure is provided on the substrate on the side opposite to the stimulation portions. Generally, there are plurality of pad structures, and the specific number can be set according to actual wiring needs.

Preferably, a processing chip is further connected onto the substrate, and the processing chip and the substrate are connected through flip-chip bonding. The processing chip can directly communicate with the stimulation electrode array, so that when wiring is conducted to the outside of an eyeball, there is no need to pull out a connecting wire from each stimulation electrode, and only the chip inside the eyeball and the processing chip outside the eyeball need to be connected.

The present invention further claims a method for manufacturing a high-density nerve stimulator, which is specifically described as follows.

A method for manufacturing a nerve stimulator, comprising the following steps:

S1 302: providing a metal underlayer, and cutting out a plurality of metal pins on the metal underlayer;

S2 304: performing glass filling between the metal pins cut out on the metal underlayer, so that the cut-out metal pins are completely covered with glass;

S3 306: performing double-sided thinning on the metal underlayer subjected to molten glass pouring, wherein the glass covering layer on the cutting side of the metal underlayer is thinned until the metal pins are exposed, and the metal underlayer on the other side of the metal underlayer is thinned and removed, until a glass substrate side formed by pouring is completely exposed; and S4 308: processing one side of the product obtained by the above step, so that the metal pins in the glass substrate form stimulation portions on the glass plane, and stimulation electrodes with a glass substrate are integrally formed.

Preferably, the cutting manner in the step S1 is laser cutting or mechanical cutting.

Preferably, the metal pins cut out in the step S1 are arranged in an array, and the shape of the array thereof may be changed according to specific stimulation needs.

Preferably, a pad structure for wiring is also cut out in the S1.

Preferably, the metal underlayer in the step S1 is made of a metal material with biocompatibility, such as titanium, platinum, iridium, tantalum, gold or an alloy thereof.

Preferably, the thermal expansion coefficient of the filling glass matches the thermal expansion coefficient of the metal underlayer.

Preferably, the thickness of the metal underlayer is between 0.3 mm and 1.5 mm, the depth of the cut-out metal pin is 200 μm to 1000 μm, and the diameter or side length of the cut-out metal pin is 50 μm to 150 μm.

Preferably, in the step S2, the specific method for embedding the metal pins in the glass is as follows:

A. selecting a glass substrate and heating it until the material thereof is softened;

B. squeezing and embedding the metal pin side of the metal underlayer from which a plurality of metal pins is cut out into the softened glass substrate, so that the metal pins are completely wrapped by the glass substrate; and C. cooling and molding.

Preferably, in the step S2, the specific method for embedding the metal pins in the glass is as follows:

A. heating glass into a melt in a molten state;

B. pouring the molten glass on the metal pin side of the metal underlayer, so that the liquid glass completely covers the metal pins; and C. cooling and molding.

Preferably, in the step S2, the specific method for performing glass filling between metal pins is as follows:

A. filling the side of the metal underlayer on which metal pins are cut out with glass powder;

B. heating the metal underlayer and the glass powder thereon, so that the glass powder is in a molten state and forms a molten glass layer on the metal underlayer; and C. cooling and molding.

The present invention has the following advantageous effects: in the present invention, a glass substrate and metal stimulation micro-electrodes are employed in the nerve stimulator, and the nerve stimulator has a high density of micro-electrodes and has a good therapeutic effect; moreover, an ultra-high density stimulation electrode array can be manufactured by using the nerve stimulation electrodes in the present invention through the method of cutting a metal underlayer, filling the underlayer with a glass layer, and then thinning and removing the metal layer to form the stimulation electrodes; and the manufacturing method adopts a novel process and a unique manner, and overcomes the deficiency in the prior art that it is rather difficult to manufacture a high density of nerve stimulation electrodes by using other substrates such as ceramics and the like.

Figure 1:
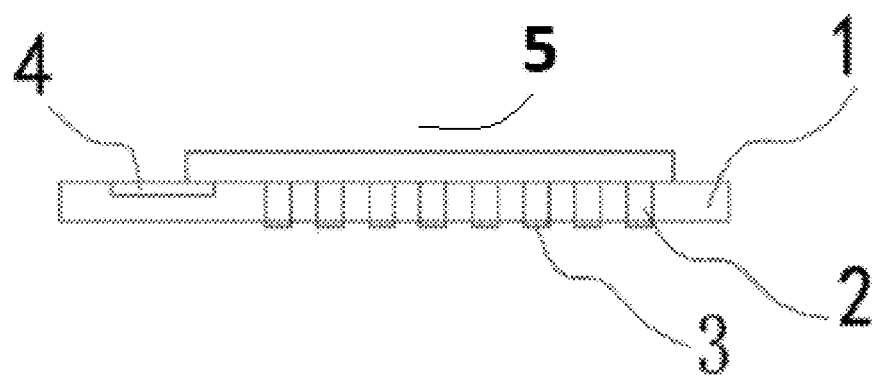
FIG. 1 is a side view of the nerve stimulator in the present invention.
Figure 2:
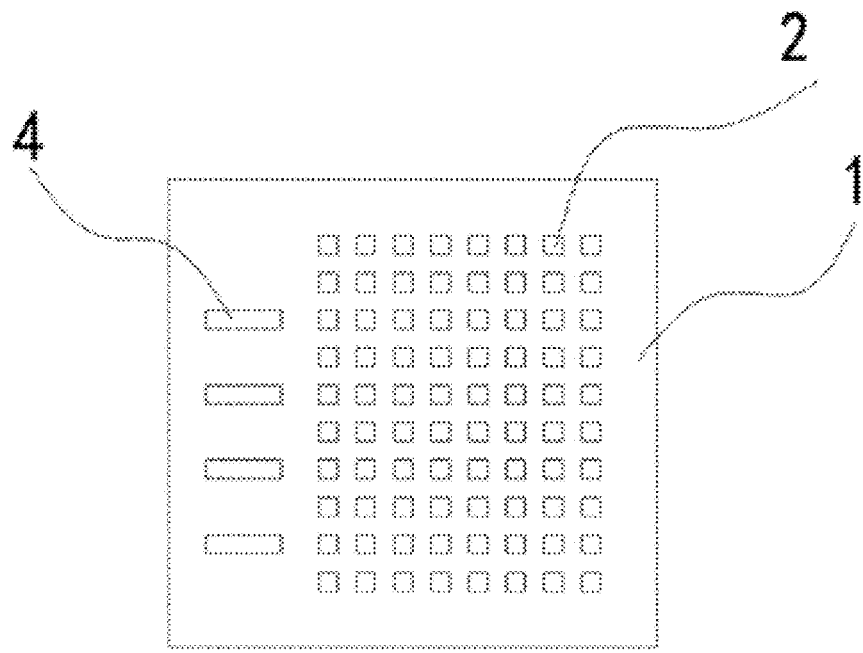
FIG. 2 is a plan view of the nerve stimulator in the present invention.
Figure 3:
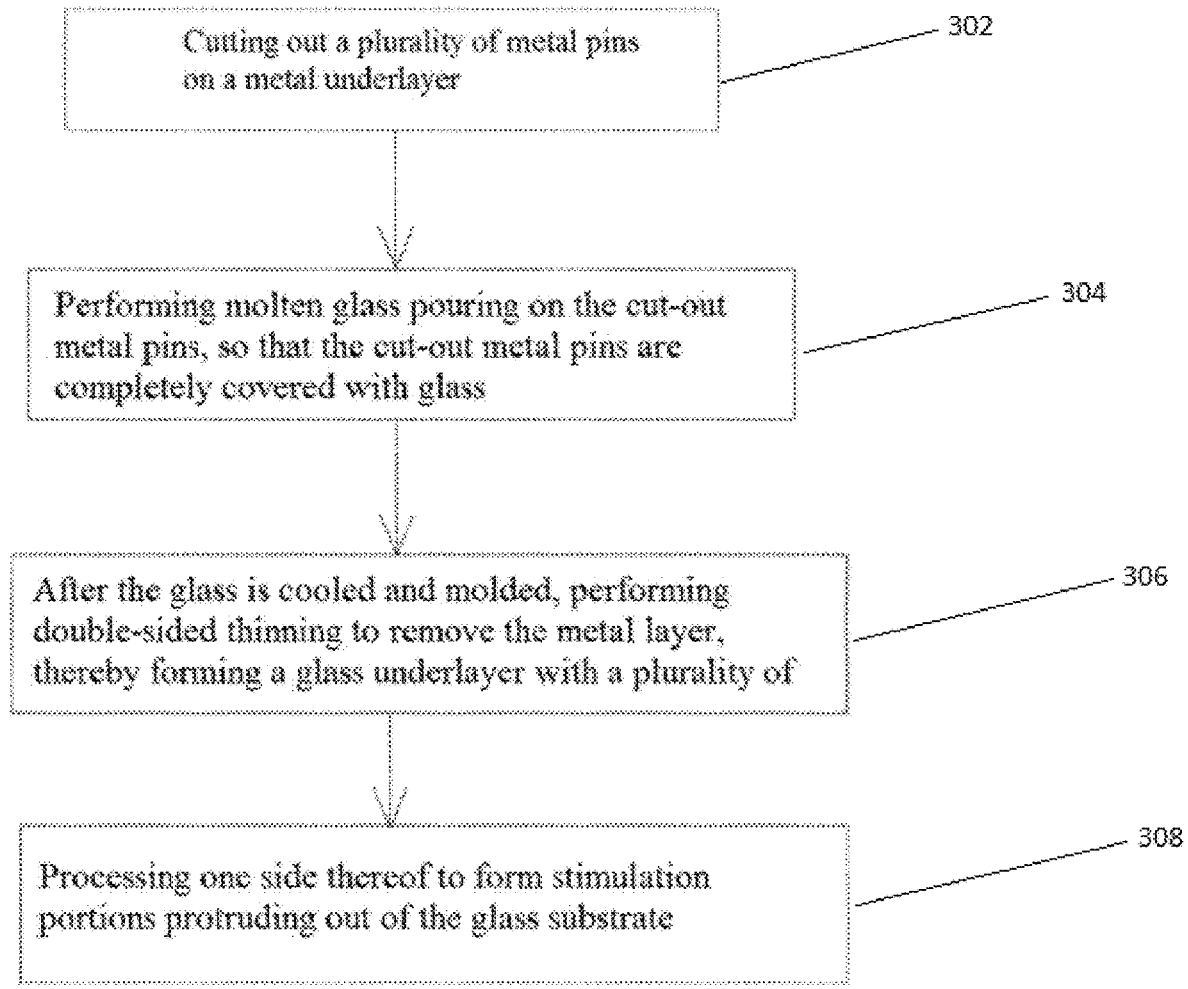
FIG. 3 is a flowchart of the method for manufacturing a nerve stimulator in the present invention.
Figure 4:
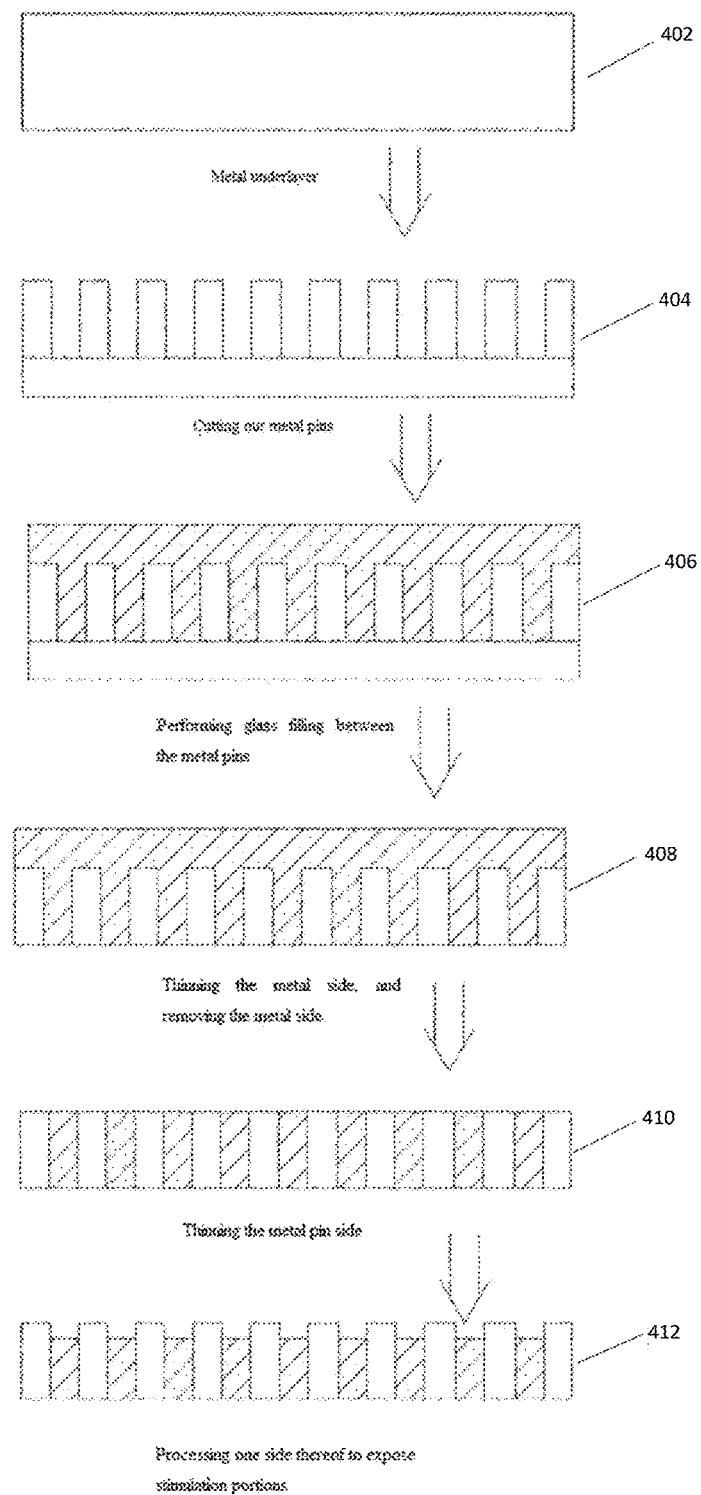
FIG. 4 is a flowchart of the method for manufacturing a nerve stimulator in the present invention.

Wherein 1 is a glass substrate, 2 is a metal pin, 3 is a stimulation portion, 4 is a pad structure, and 5 is a processing chip.

DETAILED DESCRIPTION

For the purposes of promoting an understanding of the present invention, the principle of the present invention will now be further described with reference to the attached drawings.

The present invention firstly shows a nerve stimulator, which comprises a substrate a wherein the substrate is made of a glass material, and a plurality of metal pins provided on the substrate, wherein stimulation portions are formed on one side of the metal pins, and those stimulation portions are used for stimulating human tissues.

A pad structure made of a metal material is further provided on the glass substrate, and is generally used for connecting with a chip to control the stimulation electrodes. When the nerve stimulator is used, since the pad structure needs to be in signal connection with the outside, the pad structure is generally provided on the substrate on the side opposite to the stimulation portions, which can avoid interference with the stimulation portions during wiring or packaging, and also prevent the signal connection joint from being in long-term contact with the body fluid, thereby improving the reliability thereof.

In general, the density of micro-electrodes of a nerve stimulator manufactured by using a ceramic substrate hardly exceeds 5 Pin/mm$^2$, while in the present invention, in order to make the stimulation effect better, the density of the cut-out metal pins is greater than 15 Pin/mm$^2$.

The stimulation portions formed by the metal pins protruding from the glass substrate are generally distributed in an array, and the shape of the array may be changed according to actual needs. The height of the stimulation portion is 1 to 100 μm, and the stimulation portion generally has the shape of an elongated pyramid.

As another aspect of the present invention, a method for manufacturing a nerve stimulator is also claimed, by which the above nerve stimulator having a high density of stimulation electrodes can be manufactured. The specific method is described as follows.

A method for manufacturing a nerve stimulator, comprising the following steps:

Step 1 402: providing a metal underlayer, and 404 cutting out a plurality of metal pins on the metal underlayer, wherein this cutting manner may be laser cutting or mechanical cutting, the cut-out metal pins are arranged in an array, and generally a pad structure is also cut out during the cutting;

Step 2 406: performing glass filling between the cut-out metal pins, wherein the glass is filled on the metal pins, so that the cut-out metal pins are completely covered with glass;

Step 3 408 : after the filled glass layer is cooled and molded, performing double-sided thinning on the metal underlayer that has been subjected to glass filling, wherein the glass covering layer on the cutting side of the metal underlayer is thinned until the metal pins are exposed, and the metal underlayer on the other side of the metal underlayer is thinned and removed, until a glass substrate side formed by pouring is completely exposed, in which way, the metal layer can be completely removed, 410 leaving a nerve stimulator with a glass substrate and a plurality of stimulation electrodes integrally formed thereon; and Step 4 412: after the above steps are completed, further processing one side of the product obtained by the above step, that is, removing the glass substrate around the metal pins on one side by cutting, so that the metal pins in the glass substrate protrude out of the glass plane to form stimulation portions, and stimulation electrodes with the glass substrate are integrally formed.

In the above step 2, there may be three examples below for the specific method of conducting molten glass pouring.

Example 1

Step 1: selecting a glass substrate, and heating it until the material thereof is softened;

Step 2: squeezing and embedding the metal pin side of the metal underlayer from which a plurality of metal pins is cut out into the softened glass substrate, so that the metal pins are completely wrapped by the glass substrate; and Step 3: cooling and molding.

Example 2

Step 1: heating glass into a melt in a molten state;
Step 2: pouring the molten glass on the metal pin side of the metal underlayer, so that the liquid glass completely covers the metal pins; and
Step 3: cooling and molding.

Example 3

Step 1: filling the side of the metal underlayer on which metal pins are cut out with glass powder;
Step 2: heating the metal underlayer and the glass powder thereon, so that the glass powder is deposited in a molten state on the metal underlayer and forms a molten glass layer; and
Step 3: cooling and molding.

After the above steps, it is generally necessary to further heat and squeeze the glass to reduce the gap between the glass and the metal pins.

Since the nerve stimulator needs to be implanted into a body, there are strict requirements for biocompatibility of the materials used in the nerve stimulator, and thus the metal underlayer processed to form the metal pins and the pad structure is generally made of a metal material with biocompatibility, such as titanium, platinum, iridium, tantalum, gold or an alloy thereof.

The thickness of the metal underlayer is generally between 0.3 mm and 1.5 mm, so that a proper length of the cut-out metal pin can be guaranteed, and meanwhile, the processing efficiency in the subsequent process of double-sided thinning would not be reduced, due to a too thick metal layer. Furthermore, in order to guarantee a proper thickness of the glass substrate and a proper stimulation length of the stimulation portion, the depth of the cut-out metal pin is generally 200 μm to 1000 μm, the diameter or the side length of the cut-out metal pin is 50 μm to 150 μm, and the specific numerical values thereof may vary according to actual needs.

In the subsequent operation process, since signal connection needs to be established on the nerve stimulator or the nerve stimulator needs to be bonded with a chip, the substrate needs to be heated. In order to avoid a gap formed between the glass substrate and the metal pins due to heating, the thermal expansion coefficient of the molten and poured glass needs to match the thermal expansion coefficient of the metal underlayer.

The above Examples are merely preferred examples of the present invention and are not intended to limit the present invention. It should be noted that any modifications, equivalent substitutions, or improvements made without departing from the spirit and principles of the present invention shall be included in the protection scope of the present invention.

What is claimed is:

1. A nerve stimulator, comprising a substrate, a plurality of metal pins on the substrate, wherein the metal pins run through the substrate from a first side of the substrate to a second side of the substrate and protrude from the first side to form stimulation portions, the substrate is made of a glass material, and a pad structure made of a metal material on the glass substrate.

2. The nerve stimulator according to claim 1, wherein a density of the metal pins is greater than 15 Pin/mm$^2$.

3. The nerve stimulator according to claim 1, wherein a height of the stimulation portions is 1 μm to 100 μm.

4. The nerve stimulator according to claim 1, wherein the pad structure is provided on the substrate on the second side opposite to the stimulation portions.

5. The nerve stimulator according to claim 1, wherein a processing chip is connected onto the substrate, and the processing chip and the substrate are connected through flip-chip bonding.

* * * * *